（12) United States Patent
Downs et al.

(10) Patent No.: US 6,273,575 B1
(45) Date of Patent: Aug. 14, 2001

(54) SELF INSPECTION APPARATUS

(75) Inventors: Robert R. Downs; Olena E. Downs, both of Bulverde, TX (US)

(73) Assignee: H. Mandell, San Antonio, TX (US)

( * ) Notice: Subject to any disclaimer, the term of this patent is extended or adjusted under 35 U.S.C. 154(b) by 876 days.

(21) Appl. No.: 08/590,016

(22) Filed: Jan. 25, 1996

Related U.S. Application Data

(63) Continuation of application No. 08/378,407, filed on Jan. 26, 1995, now abandoned.

(51) Int. Cl.[7] .............................. G02B 5/08; G02B 7/182
(52) U.S. Cl. .............................. 359/871; 359/896; 4/661; 600/247
(58) Field of Search ..................... 359/871, 872, 359/879, 880, 881, 896; 128/21, 22; 4/661; 600/247

(56) References Cited

U.S. PATENT DOCUMENTS

| | | | |
|---|---|---|---|
| 3,411,842 | * 11/1968 | Levy | 359/879 |
| 3,775,777 | * 12/1973 | Roberts, Jr. . | |
| 3,989,359 | * 11/1976 | Shutt | 359/872 |
| 4,257,680 | * 3/1981 | Baczkowski . | |
| 4,623,955 | * 11/1986 | Santini | 359/871 |
| 4,850,688 | 7/1989 | Rosenberg et al. . | |
| 5,301,068 | * 4/1994 | Minisci | 359/879 |
| 5,311,366 | * 5/1994 | Gerace | 359/879 |

* cited by examiner

Primary Examiner—Ricky D. Shafer

(57) ABSTRACT

A self-inspection apparatus includes a frame that supports a mirror. The frame includes first and second side members connected to first and second cross-members. The inner edges of the first and second side members and the first and second cross-members define an opening that permits access to a user's genital region. The first side member includes a first protrusion and the second side member includes a second protrusion that along with the inner edge of the first cross-member define a slot for holding the mirror. Furthermore, the first side member extends beyond the second cross-member to form a first mounting member and the second side member extends beyond the second cross-member to form a second mounting member. The inner edge of the first mounting member, the inner edge of the second mounting member, and the outer edge of the second cross-member define a curved surface that approximates the shape of a toilet bowl. Additionally, the mirror includes a first cut-out portion that defines a first stop and a second cut-out portion that defines a second stop wherein the first and second stops abut the first and second side members, respectively, when the mirror resides in the slot to hold the mirror on the frame.

7 Claims, 3 Drawing Sheets

SELF INSPECTION APPARATUS

CROSS-REFERENCE TO RELATED APPLICATIONS

This application is a continuation of application Ser. No. 08/378,407 filed on Jan. 26, 1995 and now abandoned.

BACKGROUND OF THE INVENTION

1. Field of the Invention

The present invention relates to apparatus for self-inspection of the genital region and, more particularly, by not by way of limitation, to an apparatus positionable in front of a user to provide a view of the genital region that allows the insertion of medical devices such as a catheter.

2. Description of the Related Art

U.S. Pat. No. 4,623,955 which issued Nov. 18, 1986 to Santini and U.S. Pat. No. 3,989,359 which issued Nov. 2, 1976 to Shutt disclose devices for self-examination of the genital region. Both devices are positioned within the bowl of a toilet and mount underneath the seat of the toilet using a brace. The brace supports a mirror utilized to perform the self-inspection of the genital region. A user sits on the toilet seat towards the rear and inspects herself using the mirror supported by the brace.

Although the actual use of both self-inspection devices is uncomplicated, the positioning of the devices in the center of toilet bowl precludes their use for the insertion of a medical device such as a catheter. That is, the user cannot access her genital area with her hands for the insertion of a medical device because the positioning of the self-inspection devices directly in front and slightly beneath the user's genital region blocks any such access.

U.S. Pat. No. 5,311,366 which issued May 10, 1994 to Gerace and U.S. Pat. No. 4,257,680 which issued Mar. 24, 1991 to Baczkowski disclose self-inspection devices that mount to a user's leg(s) to place the inspection mirror in front of the genital area. These devices, unfortunately, require the user to either sit or lay in an awkward position during the insertion of a medical device. Furthermore, when using either device, the user's movements are strictly limited. That is, both devices require the user maintain the same position at all times during the insertion of a medical device to maintain the mirror focused on the genital region. The necessity that body rigidity be maintained causes great difficulty during the insertion of a medical device because minor shifts in body position that permit easier insertion of the device may not be performed.

U.S. Pat. No. 5,301,068 which issued Apr. 5, 1994 to Minisci discloses a self-inspection device including a free-standing frame that supports the inspection mirror. The device is placed in front of a chair and the free-standing frame adjusted to place the mirror in front of the user's genital area. Although the self-inspection device operates adequately, it is somewhat complicated to use because the free-standing frame must be assembled and then adjusted before each use.

Accordingly, a self-inspection apparatus that permits the user easy access to her genitals for the insertion of a medical device such as a catheter while remaining of simple construction is highly desirable.

SUMMARY OF THE INVENTION

In accordance with the present invention, a self-inspection apparatus includes a frame that supports a mirror. The frame includes first and second side members connected to first and second cross-members. The inner edges of the first and second side members and the first and second cross-members define an opening that permits access to a collection bottle after catheterization. The first side member includes a first protrusion and the second side member includes a second protrusion that along with the inner edge of the first cross-member define a slot for holding the mirror. Furthermore, the first side member extends beyond the second cross-member to form a first mounting member and the second side member extends beyond the second cross-member to form a second mounting member. The inner edge of the first mounting member, the inner edge of the second mounting member, and the outer edge of the second cross-member define a curved surface that approximates the shape of a toilet bowl. Additionally, the mirror includes a first cut-out portion that defines a first stop and a second cut-out portion that defines a second stop wherein the first and second stops abut the first and second side members, respectively, when the mirror resides in the slot to hold the mirror on the frame.

It is, therefore, an object of the present invention to provide a self-inspection apparatus that mounts to the front of a toilet.

It is another object of the present invention to provide a self-inspection apparatus with a mirror positioned in front of the user and angled to provide easy visual inspection.

It is further object of the present invention to provide a self-inspection apparatus that provides a user easy access to her genitals during viewing to permit the insertion of a medical device such a catheter.

Still other objects, features, and advantages of the present invention will become evident to those skilled in the art in light of the following.

DETAILED DESCRIPTION OF THE PREFERRED EMBODIMENT

Figure 1B:
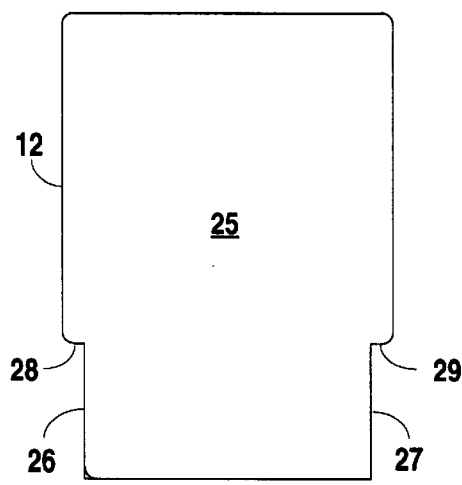
FIG. 1B is a top plan view illustrating the mirror for the self-inspection apparatus.
Figure 1A:
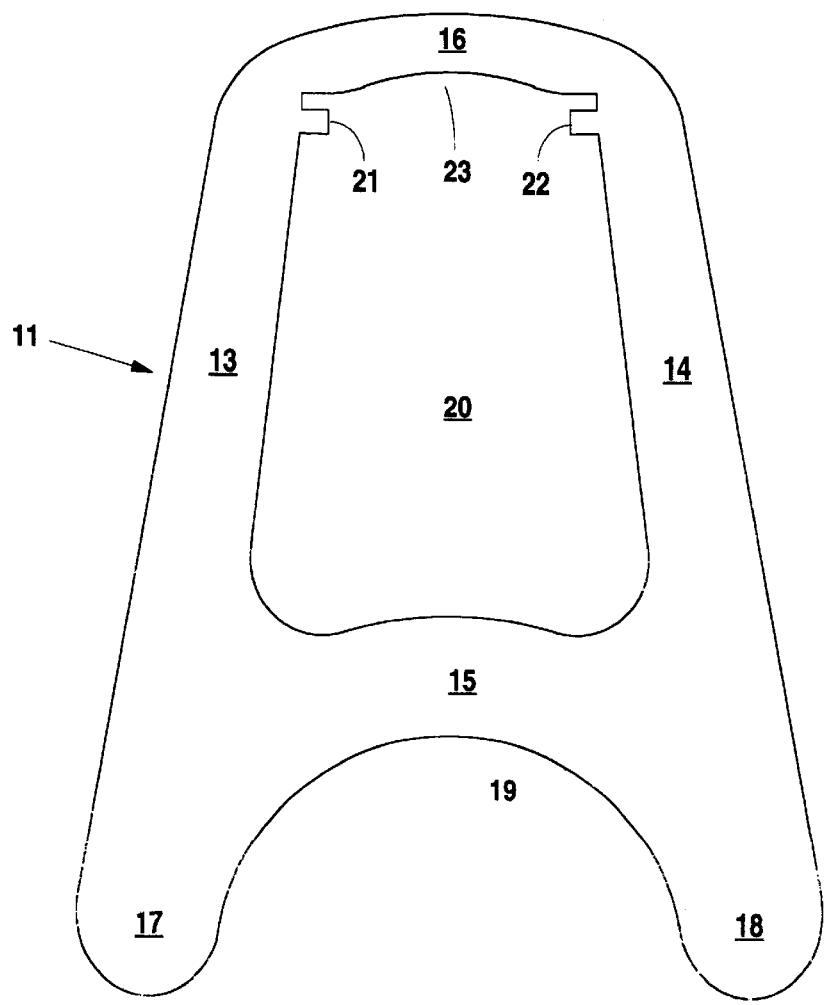
FIG. 1A is a top plan view illustrating the frame for the self-inspection apparatus.
Figure 2:
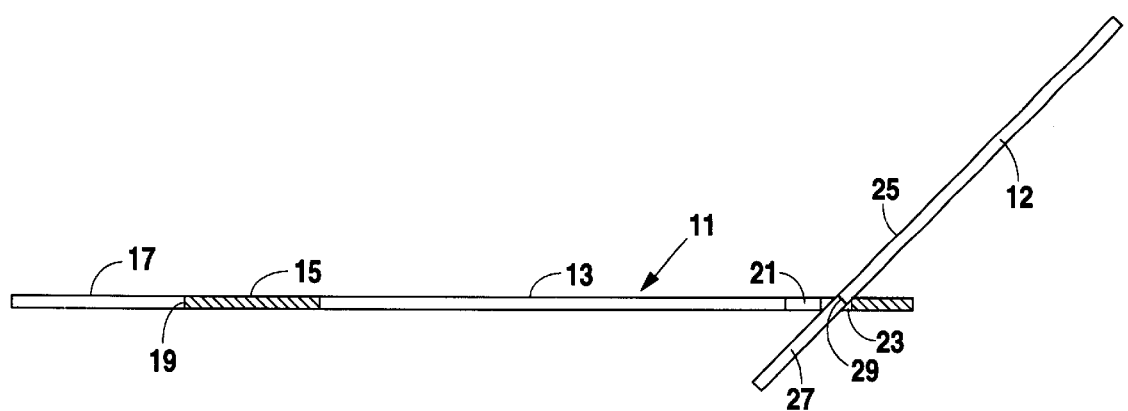
FIG. 2 is a side plan view in cross-section illustrating the mounting of the mirror onto the frame.

As illustrated in FIGS. 1A, 1B, and 2, self-inspection apparatus 10 includes frame 11 and mirror 12. In this preferred embodiment, frame 11 is constructed from polyethylene to provide a frame with sufficient rigidity to support mirror 12 while maintaining sufficient flexibility to prevent easy breakage. The preferred method of forming frame 11 is cutting frame 11 from a piece of the polyethylene using a pattern as a guide.

Frame 11 includes side members 13 and 14 formed integrally with cross-members 15 and 16. Cross-member 16 forms an integral connection between one set of ends of side member 13 and 14. The opposite ends of side members 13 and 14 extend beyond cross-member 15 to form mounting members 17 and 18. The inner edges of mounting members 17 and 18 along with the outer edge of cross-member 15 define curved surface 19 that approximates the curvature of a toilet bowl. The inner edges of side members 13 and 14 and cross-members 15 and 16 define opening 20 that provides a space allowing easy access to a collection bottle for measuring urine after catheterization. Side members 13 and 14 include protrusions 21 and 22, respectively, that along with the inner edge of cross-member 16 define slot 23.

In this preferred embodiment, mirror 12 is constructed from polycarbonate to provide a flexible material that will not easily break. Mirror 12 includes reflective surface 25 to permit a user to examine her genitals. Mirror 12 includes cut-out portions 26 and 27 that define stops 28 and 29, respectively. Mirror 12 mounts onto frame 11 by sliding the lower portion of mirror 12 through slot 23 until stops 28 and 29 engage side members 13 and 14, respectively (see FIG. 2). In that position, mirror 12 is angled with reflective surface 25 facing upwards to permit easy viewing of the genital region by a user of self-inspection apparatus 10.

Figure 3:
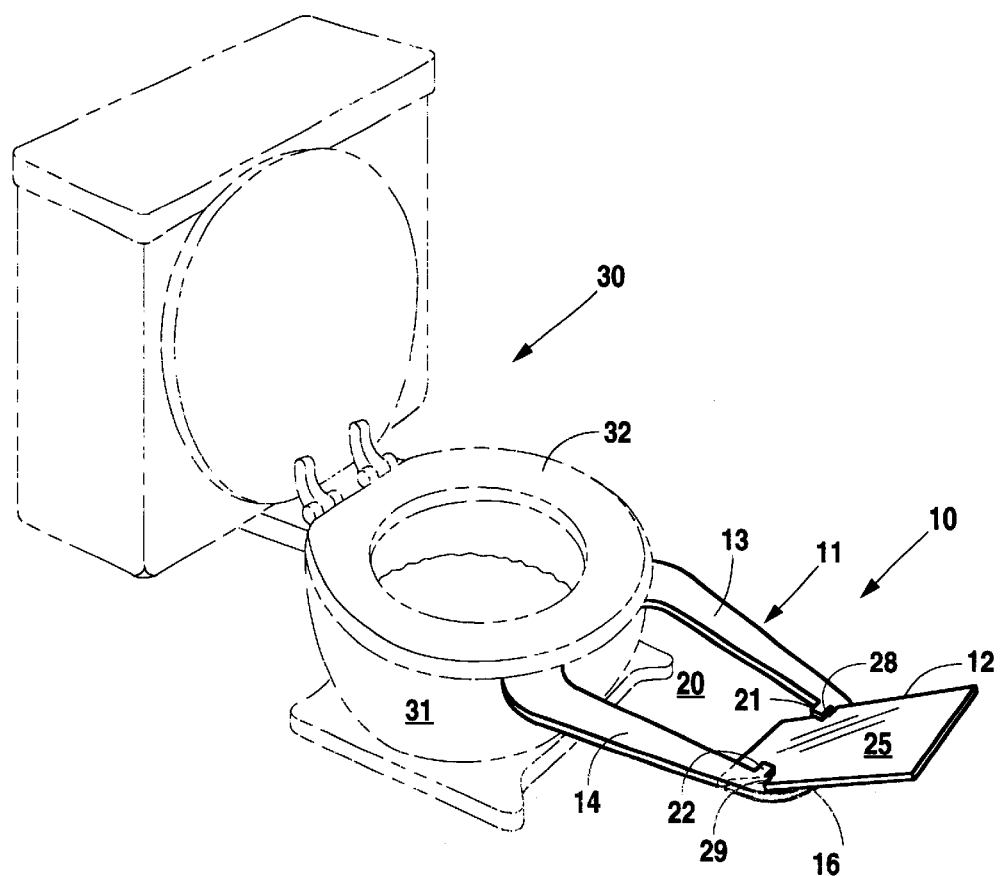
FIG. 3 is a perspective view illustrating the mounting of the self-inspection apparatus on a toilet.
Figure 4:
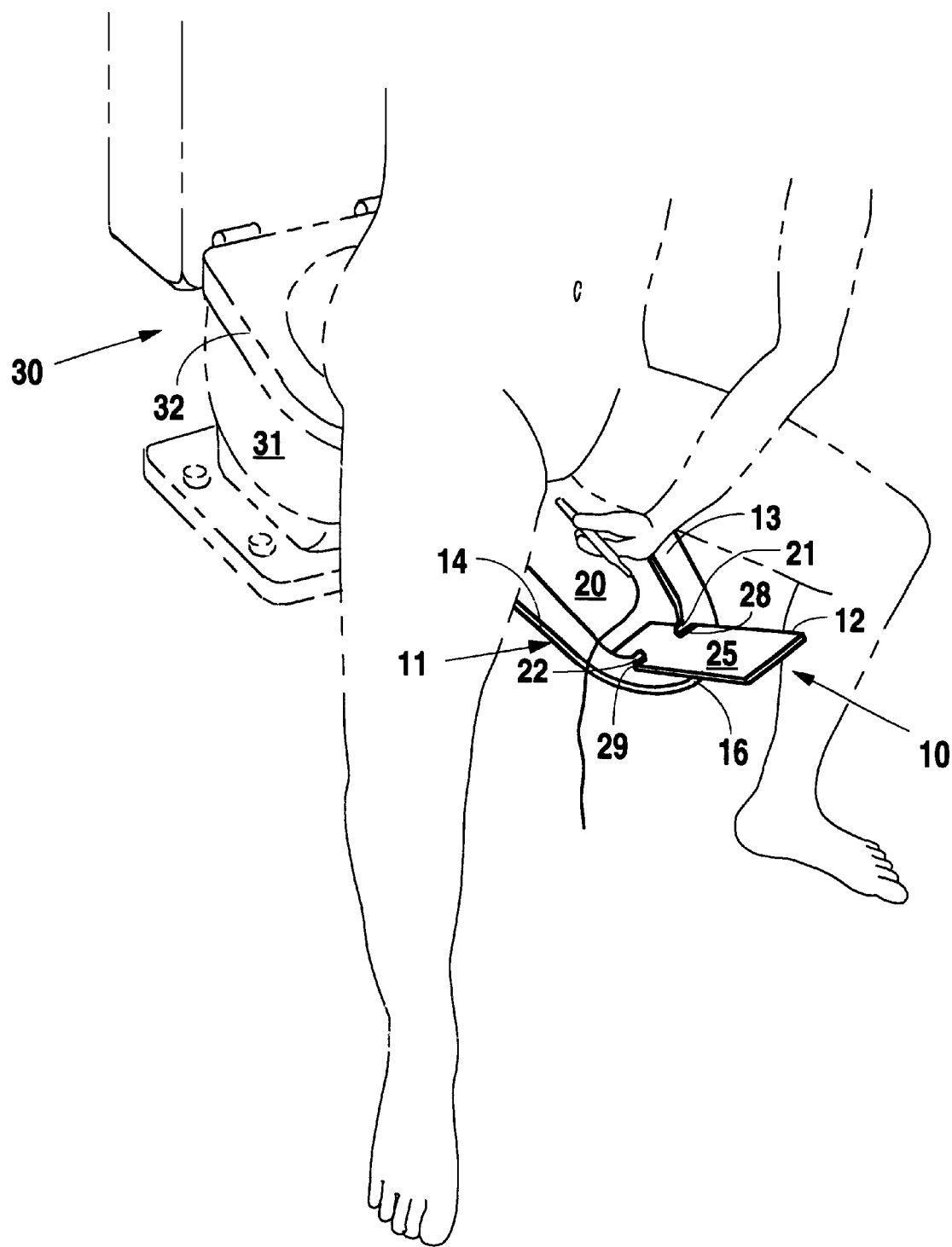
FIG. 4 is a perspective view illustrating the position of a user with respect to the self-inspection apparatus.

As illustrated in FIGS. 3 and 4, self-inspection apparatus 10 mounts to the front of toilet 30 to permit a user to examine her genital region during the insertion of a medical device such as a catheter. Frame 11 is held parallel to bowl 31 of toilet 30 such that cross-member 15 and mounting members 17 and 18 reside at the front of bowl 31 over its top edge. Seat 32 is then lowered to its normal down position which holds frame 11 secured at the front of toilet 30. Mirror 12 may be mounted on frame 11 as previously described if it was not done previously. The user then sits on seat 32 towards the front so that her genital region may easily be seen in reflective surface 25 of mirror 12. Opening 20 through frame 11 permits the user easy access to a collection bottle for urine measurement after catheterization. Additionally, the user may shift her position at any time during the insertion of the medical device because the size of mirror 12 and its position in front of the user at an angle permits significant movement without the user losing sight of her genital region.

Although the present invention has been described in terms of the foregoing embodiment, such description has been for exemplary purposes only and, as will be apparent to one of ordinary skill in the art, many alternatives, equivalents, and variations of varying degrees will fall within the scope of the present invention. That scope, accordingly, is not to be limited in any respect by the foregoing description, rather, it is defined only by the claims that follow.

We claim:

1. A self-inspection apparatus, comprising:
   a mirror; and
   a frame placeable along the front edge of a toilet bowl and secured thereto by a toilet seat for holding said mirror in front of the exterior surface of the toilet bowl in a position facing the toilet bowl.

2. The self-inspection apparatus according to claim 1 wherein said frame comprises first and second side members connected to first and second cross-members.

3. The self-inspection apparatus according to claim 2 wherein the inner edges of said first and second side members and said first and second cross-members define an opening that permits access to a collection bottle after catheterization.

4. The self-inspection apparatus according to claim 2 wherein said first side member includes a first protrusion and said second side member includes a second protrusion that along with the inner edge of said first cross-member define a slot for holding said mirror.

5. The self-inspection apparatus according to claim 4 wherein said mirror includes a first cut-out portion that defines a first stop and a second cut-out portion that defines a second stop wherein said first and second stops abut said first and second side members, respectively, when said mirror resides in said slot to hold said mirror on said frame.

6. The self-inspection apparatus according to claim 2 wherein said first side member extends beyond said second cross-member to form a first mounting member and said second side member extends beyond said second cross-member to form a second mounting member.

7. The self-inspection apparatus according to claim 6 wherein the inner edge of said first mounting member, the inner edge of said second mounting member, and the outer edge of said second cross-member define a curved surface that approximates the shape of a toilet bowl.

* * * * *